United States Patent
Lang et al.

(10) Patent No.: US 7,235,364 B2
(45) Date of Patent: Jun. 26, 2007

(54) ClCKB MUTATION AS A DIAGNOSTIC AND THERAPEUTICAL TARGET

(75) Inventors: Florian Lang, Tuebingen (DE);
Siegfried Waldegger, Marburg (DE);
Philipp Lang, Tuebingen (DE);
Angelika Lampert, Tuebingen (DE);
Hannsjoerg Seybert, Marburg (DE);
Nikola Jeck, Marburg (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 0 days.

(21) Appl. No.: 11/398,208

(22) Filed: Apr. 4, 2006

(65) Prior Publication Data
US 2006/0240459 A1    Oct. 26, 2006

Related U.S. Application Data

(62) Division of application No. 10/687,523, filed on Oct. 15, 2003, now Pat. No. 7,074,573.

(51) Int. Cl.
*C12Q 1/68* (2006.01)
(52) U.S. Cl. .......................................... 435/6
(58) Field of Classification Search ............... 435/6
See application file for complete search history.

(56) References Cited

FOREIGN PATENT DOCUMENTS

WO    WO 99/16909 A1    4/1999
WO    WO 01/73128 A1    10/2001

OTHER PUBLICATIONS

Jeck et al. 2004; Activating mutation of the renal epithelial chloride channel ClC-Kb predisposing to hypertension. Hypertension 43: 1175-1181.*
Speirs et al. 2005; No association with hypertension of CLCNKB and TNFRSF1B polymorphisms at a hypertension locus on chromosome 1p36. Journal of Hypertension 23: 1491-1496.*
Jeck, N. et al. (2003) "Functional importance of CLCNKB genetics variants" *Pediatric Nephrology*, 18:13C.
Jeck, N. et al. (2003) "A common sequence variation of the CLCNKB gene strongly activates CLC-KB chloride channel activity (W22)" *Nephrology Dialysis Transplantation* Oxford 18:555.
Kieferle, S. et al. (1994) "Two highly homologous members of the ClC chloride channel family in both rat and human kidney" *PNAS USA* 91:6943-6947.
Konrad, M. et al. (2000) "Mutations in the chloride channel gene ClCNKb as a cause of classic barter syndrome" *J. Am. Soc. Nephrol.* 11:1449-1459.
Simon, D.B. et al. (1999) "*Homo sapiens* chloride channel Kb (CLCNKB) mRNA" Database Genebank (1999) "Online! NCBI: XP002314410.
Simon, D.B. et al. (1997) "Mutations in the chloride channel gene, ClCNKb, cause bartter's syndrome type III" *Nature Genetics* 17:171-178.
International Search Report from co-pending application PCT/EP2004/011192.
Written Opinion from co-pending application PCT/EP2004/011192.

* cited by examiner

*Primary Examiner*—Karen Cochrane Carlson
(74) *Attorney, Agent, or Firm*—Knobbe, Martens, Olson & Bear LLP

(57) ABSTRACT

The present invention relates to a method for diagnosing hypertension, and/or allergy, and/or hair loss, and/or liabilty for infection, of a human being, or a predisposition therefor; to a nucleic acid molecule coding for a human ClCKb protein comprising a genetic alteration at amino acid position 481 compared to the wild type, as well as for corresponding segments thereof; to a nucleic acid molecule which binds to the before-mentioned nucleic acid molecule under stringent conditions, as well as to a nucleic acid molecule which binds to that nucleic acid molecule; to a (poly)peptide encoded by the afore-mentioned nucleic acid molecules; to a method for identifying substances modulating activity of a peptide derived from ClCKb protein that is genetically altered at amino acid position 481 compared to the wild type; to a substance for modulating activity of a peptide derived from ClCKb protein that is genetically altered at amino acid position 481 compared to the wild type; to methods for preparing a pharmaceutical composition for treatment of hypertension, and/or allergy, and/or hair loss, and/or liability for infection; to pharmaceutical compositions; and to a method for treating a human being affected by hypertension, and/or allergy and/or hair loss, and/or liability for infection.

6 Claims, 1 Drawing Sheet

ClCKB MUTATION AS A DIAGNOSTIC AND THERAPEUTICAL TARGET

RELATED APPLICATIONS

This application is a divisional of U.S. patent application Ser. No. 10/687,523, filed on Oct. 15, 2003, now U.S. Pat. No. 7,074,573.

BACKGROUND OF THE INVENTION

1. Field of the Invention

The present invention relates to a method for diagnosing hypertension, and/or allergy, and/or hair loss, and/or liability for infection, of a human being, or a predisposition therefor; to a nucleic acid molecule coding for a human ClCKb protein comprising a genetic alteration at amino acid position 481 compared to the wild type, as well as for corresponding segments thereof; to a nucleic acid molecule which binds to the before-mentioned nucleic acid molecule under stringent conditions, as well as to a nucleic acid molecule which binds to that nucleic acid molecule; to a (poly)peptide encoded by the afore-mentioned nucleic acid molecules; to a method for identifying substances modulating activity of a peptide derived from ClCKb protein that is genetically altered at amino acid position 481 compared to the wild type; to a substance for modulating activity of a peptide derived from ClCKb protein that is genetically altered at amino acid position 481 compared to the wild type; to methods for preparing a pharmaceutical composition for treatment of hypertension, and/or allergy, and/or hair loss, and/or liability for infection; to pharmaceutical compositions; and to a method for treating a human being affected by hypertension, and/or allergy and/or hair loss, and/or liability for infection.

2. Related Prior Art

Methods of these afore-mentioned kinds in general are known in the art.

About 20% of the population of Western industrial nations are suffering from high blood pressure. Subsequent illnesses such as apoplectic stroke, cardiac infarction, renal insufficiency, and peripheral circulatory disorders belong to the most frequently causes of death. Up to now the cause for high blood pressure can be uncovered in less than 10% of the high blood pressure patients, as being an endocrine disorder (ca. 1%) or a kidney disease (ca. 7%). If no cause can be found, one speaks of an essential hypertension. If hypertension appears in a familial cumulative manner then evidence is given for the existence of genetic defects. Actually, up to now several monogenetic diseases leading to hypertension have been discovered.

For example, in the Liddle's syndrom a mutation of the renal $Na^+$ channel ENaC has been identified which causes an increased activity of that channel (gain of function mutation); cf. Hansson J. H. et al. (1995), *Nat Genet* 11, 76–82; Lifton R. P. (1996), *Science* 272, 676–680; Schild L. et al. (1996), *EMBO J* 15, 2381–2387. In the so-called Gordon syndrome a mutation of a kinase leads to an overactivity of the renal NaCl co-transporter; Wilson F. H. et al. (2001), *Science* 293, 1107–1112. Mutations of the mineral corticoid receptors, Geller D. S. (1998), *Nat Genet* 19, 279–281, cf. Geller D. S. et al. (2000), *Science* 289, 119–123, or of the cortisole degrading enzyme 11-β-hydroxy steroid dehydrogenase, cf. Mune T. et al. (1995), *Nat Genet* 10, 394–399; Stewart P. M. et al. (1996), *Lancet* 347, 88–91, and the glucocortocoid remediable hypertension, Lifton R. P. et al. (1992), *Nature* 355, 262–265, Lifton R. P. et al. (1992), *Nat Genet* 2, 66–74, lead to hypertension via increased activity of ENaC. All of these diseases are extremely rare. An overview about the current knowledge concerning the genetics of rare forms of hypertension is given in Staessen et al. (2003), *Lancet* 361, 1629–1641.

On account of lacking of genetic information regarding widespread forms of hypertension up to now hypertension is usually diagnosed via blood pressure measurements, i.e. hemodynamometry, normally via the method according to Riva-Rocci.

This common method for diagnosing hypertension has several disadvantages. Firstly, blood pressure measurements, of course, give no information about the physiological and medical cause of a diagnosed hypertension. Secondly, because of lacking of knowledge about the cause of a diagnosed hypertension the basis for a goal-orientated therapy or prevention is not given. Thirdly, by common blood pressure measurements only an existing or acute hypertension will be identified, e.g. not a predisposition therefor.

SUMMARY OF THE INVENTION

Against this background a problem underlying the present invention is to provide a method for diagnosing hypertension by which the afore-mentioned disadvantages will be avoided. Especially, such a method should be provided by means of which hypertension can be diagnosed via a genetic alteration compared to the wild type, so that, at, the same time a basis for a goal-orientated causal therapy is given.

This problem underlying the present invention is completely solved by providing a method for diagnosing hypertension of a human being, or a predisposition therefor, comprising the steps of: a) providing a biological sample of said human being; b) analyzing said biological sample for the presence of a nucleic acid molecule, and c) correlation of positive findings to hypertension or a predisposition therefor, wherein said nucleic acid molecule is coding for a human ClCKb protein comprising a genetic alteration at amino acid position 481 compared to the wild type, as well as for corresponding segments thereof.

The inventors have realized for the first time that this genetic alteration in the ClCKb protein is responsible for the incidence of hypertension in up to 20% of the Caucasian population. Surprisingly, during the experiments leading to the invention the inventors also have discerned that individuals carrying this genetic alteration also are affected by allergy, and/or hair loss, and/or liability for infection. Hence, the method according to the invention is also suitable for diagnosing the afore-mentioned physiological disorders or a predisposition therefor, wherefore a corresponding employment of the above-described method is also an object of the present invention.

The finding of the inventors that the mentioned genetic alteration is causative for these disorders is completely surprising, since the affected ClCKb protein so far has mostly been described in totally different connections.

ClCKb is a member of the ClC family of chloride channels and participates in the renal re-absorption of NaCl; cf. Waldegger S. and Jentsch T. J. (2000), *J Am Soc Nephrol* 11, 1331–1339. The functional expression of ClCKa as another member of the ClC family, and of ClCKb channels, requires the co-expression of barttin, which thus is an essential β subunit of these channels; cf. Estevez R. et al. (2001), *Nature* 414, 558–561. The functional significance of both, ClCKb and barttin is illustrated by rare monogenic disorders. The entire nucleotide and amino acid sequence (SEQ ID NO: 1) of human ClCKb is disclosed in GenBank NCBI, Accession number NM_000085.

Defects of the ClCKb gene LICNKB underlie so-called Bartter syndrome type III, characterized by renal salt loss and hypotension; cf. Simon D. B. et al. (1997) *Nat Genet* 17, 171–178. Defects of the barttin gene BSND (Bartter syndrome with sensorineural deafness) cause Bartter syndrome type IV, characterized by congenital deafness and renal failure; cf. Birkenhager R. et al. (2001), *Nat Genet* 29, 310–314.

The inventors of the present invention themselves presented data concerning a sequence variation in the ClCKb gene, comparable to that on which the method according to the invention is based on, namely a ClCKb$^{T481S}$ amino acid exchange mutation that leads to a strongly activated ClCKb chloride channel activity, cf. Jeck N., Waldegger S. et al. (2003), World Congress of Nephrology, Berlin, Abstract Book. By the authors it has been assumed that this ClCKb$^{T481S}$ mutation is involved in blood pressure regulation. However, no evidences are provided that the mutation correlates with hypertension. Not the more, nothing is said about a possible correlation between the newly found genetic alteration and allergy, hair loss and the liability for infection.

In addition to the newly found correlation, the inventors have further realized that for a reliable correct diagnosis one has not necessarily to analyze the sample for the presence of a nucleic acid molecule coding for the entire genetically altered ClCKb protein, since it is sufficient to analyze for the presence of a nucleic acid molecule coding for a segment of the altered ClCKb protein, provided that an amino acid position is covered which corresponds to position 481 of the whole protein. According to the invention the term "corresponding segments thereof" has to be understood in this sense.

According to the invention, the term "hypertension" stands for a physiological condition of an individual, characterized by high blood pressure. Therefore, the term covers acute hypertension, characterized by a systolic blood pressure which is consistently over 140, and/or a diastolic blood pressure which is consistently over 90. Furthermore, it covers pre-hypertension characterized by a systolic blood pressure between 120 and 139 and/or a diastolic blood pressure between 80 and 89; cf. the new NHLBI Hypertension Standards (National Heart, Lung, and Blood Institute; see NHLBI website at NIH).

According to the invention, "allergy" is to be understood as a hypersensivity of the body's immune system in response to exposure to specific substances (antigens), such as pollen, beestings, poison ivy, drugs, nutrients etc.

In the sense of the invention "hair loss" is to be understood as a physiological condition characterized by unusual loss of hair or baldness of an individual, compared to average healthy individuals having comparable age, sex and physical condition.

According to the invention, "liability for infection" means that the affected individual has a tendency for suffering from viral, bacterial, fungal, protozoic or worm etc. infections, compared to average healthy individuals having comparable age, sex and physical condition.

The biological sample can be provided in any conceivable form, e.g. as tissue sample, a body liquid such as blood, saliva, sperm, and comparable. liquids, subject to the condition that representative nucleic acid material and/or protein of the human being is contained within that sample.

Step (b) is performed by means of molecular biological methods well known by a skilled person, e.g. DNA isolation, electrophoresis, PCR technology, nucleic acid sequencing, mutation analysis etc. Such methods are, e.g., described in Sambrook and Russell (2001), "Molecular Cloning—A Laboratory Manual", 3. sup.rd edition, Cold Spring Harbor Laboratory Press, which is herewith incorporated by reference.

According to a preferred embodiment, the genetic alteration is an amino acid exchange, preferably by which a threonine molecule is changed for a serine molecule (ClCKb$^{T481S}$).

That measure has the advantage that pursuant the inventors findings herewith apparently the most important genetic alteration of the ClCKb protein at amino acid position 481 causing the mentioned disorders are detected. Therefore, additional certainty and reliability concerning a correct diagnosis is ensured.

It is preferred if in step (b) of the method according to the invention such a nucleic acid molecule is detected which binds to the afore-mentioned nucleic acid molecules under stringent conditions.

Herewith also such nucleic acid molecules are pulled up for diagnosis which not necessarily code for the altered ClCKb protein, but e.g. correspond to the complementary strand and therefore indicate the genetic alteration as well. The method according to the invention is herewith further increased in sensitivity, e.g. if the biological sample is analyzed for the presence of this complementary non-coding strand beside analyzing for the presence of the coding strand.

By stringent conditions such experimental conditions are to be summarized by which only almost perfectly base-paired nucleic acid strands are formed and remain stable in that state. These conditions depend on the salt concentration, temperature, pH value etc., and are well-known to those skilled in the art.

It is preferred if in step (b) the biological sample is analyzed for the presence of such a nucleic acid molecule that binds to the directly afore-mentioned nucleic acid molecule under stringent conditions.

By this measure not only exclusively coding sequences are pulled up for diagnosis, but also sequences comprising additional nucleotides, e.g. at the 3' and/or 5' ends of the coding region or sequences comprising intronic segments, like genomic DNA or immature mRNA and the like. Therewith, the method according to the invention is further increased in sensitivity and its scope of application.

Due to their importance as a diagnostic and/or therapeutic target further objects of the present invention are likewise the afore-mentioned nucleic acid molecules to be detected in the biological sample. Such molecules establish the basis not only for molecular genetic diagnostics concerning hypertension, allergy, hair loss, or liability for infection, but also for development of highly effective pharmaceutic substances. By means of these (coding) nucleic acid molecules the genetically altered protein can be produced in large amounts and therefore can be used, e.g. for high through put or in silico-screening of pharmaceutically effective substances interacting with that genetically altered protein.

In the method according to the invention it is preferred if said analyzing for the presence of said nucleic acid molecule in step (b) is performed by means of PCR technology.

This measure has the advantage that herewith a highly sensitive, established, and largely automatable method is used, by which the genetically altered nucleic acid material can be amplified, that in turn can be detected by further standard methods such as electrophoresis or HPLC techniques.

It is further preferred if the PCR amplification products are analyzed by means of denaturing high pressure liquid chromatography (dHPLC).

The dHPLC is a method by which sequence variations in PCR amplification products compared to the wild type sequence can be selected in a highly sensitive manner. The detection bases on a heteroduplex which is formed if beside the wild type ClCKb allele also the newly found sequence variation is present on the second allele. Via preceding PCR a heteroduplex is formed with high reliability, consisting of one strand of the wild type ClCKb allele and of one strand of the genetically altered ClCKb allele. These hybrids show different retention behavior compared to a homoduplex, and can be detected with a likelihood of about more than 95%. The analysis time for one fragment is about 4 to 5 minutes, as to enable a very cost- and time-effective screening method, e.g. before an additional sequencing of the amplification products. Information about that method are e.g. given in McCallum C. M. et al. (2000), *Nature Biotechnology* 18, 455–457.

The inventors further have realized that within step (b) of the method according to the invention it is an advantageous measure to analyze the biological sample for the presence of a (poly)peptide encoded by any of the afore-said (coding) nucleic acid molecules. This alternatively configurated method is also an object of the present invention.

The (poly)peptide which is bringing out the genetic alteration is the biochemical realization of the underlying genetic information and is therefore also a suitable candidate for diagnosing the said disorders. For this purpose analyzation according to (b) is performed by means of molecular biological methods mentioned further above, especially by protein purification or sequencing methods which are also well known to those skilled in the art. The detection of the genetically altered protein is advantageous because of its increased stability compared to nucleic acids. Therefore precise diagnosis via analyzing for the presence of the (poly)peptide is still possible, even if the coding nucleic acid has been degraded, e.g. by nucleases.

Against this background a further object of the present invention relates to such a (poly)peptide encoded by any of the afore-mentioned (coding) nucleic acid molecules. As explained for the coding nucleic molecules further above, such a (poly)peptide is a suitable tool for developing effective pharmaceutical substances capable of binding to the genetic altered protein, e.g. by means of in silico-screening.

A further object of the present invention concerns a method for identifying substances modulating activity of a peptide derived from ClCKb protein that is genetically altered at amino acid position 481 compared to the wild type, comprising the steps of: (a) contacting of said peptide to a test substance, under conditions allowing the binding of that test substance to that peptide, and (b) determination, whether said test substance modulates the activity of said peptide, whereby said genetic alteration preferably is an amino acid exchange, preferably by which a threonine molecule is changed for a serine molecule (ClCKb$^{T481S}$).

Herewith a method is provided by which substances can be identified for the first time that have the potential for being causally acting agents against hypertension, allergy, hair loss or liability for infection.

According to that new method, test substances have to bind the peptide derived from the genetically altered ClCKb protein, i.e. a state has to be established in which the substance to be tested is at least in the immediate vicinity of the peptide, and therefore is possibly capable of influencing the activity of the peptide.

Modulating the activity" means that the peptide is somehow altered in its biochemical/physiological function, whether it is increased or decreased in its activity.

The determination in step (b) is performed by the observation of binding of the test substance to the peptide, if applicable additionally by the observation of an alteration in the peptides' activity by means of a well-established assay for measuring activity of ion channels, e.g. electrophysiological measurements.

The substance to be tested can be present in any chemical, biochemical, or biological form conceivable, i.e. as a molecule, like a chemical defined compound or a peptide, protein, antibody, aptamer or else an ion or an atom.

Conditions allowing the binding of the test substance to the peptide are well-known in the area of protein or enzyme biochemistry; those conditions can be provided, for example, by the usage of common physiological or biological buffer systems like Tris-Hepes-, PBS-based buffers, if applicable, supplemented with various kinds of salts in appropriate concentrations as well as with other conventional additives.

In that method it is preferred if said determination in step (b) is performed via ion current measurements, preferably via chloride ion current measurements, across a biological cell membrane, whereby it is further preferred if said ion current measurements are performed via patch clamp and/or voltage clamp technology.

These measures have the advantage that herewith a well-established experimental set-up is provided that enables measurements of the physiological activity of isolated ion channels in vitro, influenced by the substance to be tested. An adequate system is the *Xenopus* oocyte system. Herewith genetic information coding for the altered ClCKb chloride channel, e.g. cRNA encoding ClCKb$^{T481S}$ is injected into *Xenopus* oocytes, together with necessary co-factors like the barttin protein. The produced and assembled mutated chloride channel will be incorporated into the cell membrane and can be subjected to patch clamp and/or voltage clamp analysis.

In that method it is preferred if in step (b) it is determined whether said test substance inhibits ion current across said biological cell membrane.

Herewith mostly interesting pharmacological substances can be identified, since in accordance with the findings of the inventors the newly found mutation causes a significant increase of ClCKb induced ion currents, bringing about increased blood pressure, allergies, hair loss, and liability for infection. It is therefore of substantial interest to provide a substance that inhibits increased ion current. By that preferred embodiment of the aforementioned method according to the invention the desire for such a substance is met in a simple manner.

Furthermore, substances modulating activity of a peptide derived from ClCkb protein can be identified by cell volume measurements and/or measurements of cell lysis on cells overexpressing the genetically altered and/or the wild type peptide mentioned afore. By means of those methods it can be determined whether a test substance would have an influence on cell volume and/or cell lysis.

Due to its immense pharmacological importance for treating hypertension, allergy, hair loss and liability for infection, a further object of the present invention relates to a substance for modulating activity of a peptide derived from ClCKb protein that is genetically altered at amino acid position 481 compared to the wild type, identified by means of the before-mentioned "identifying" method, and also relates to a method for preparing a pharmaceutical composition, comprising the steps of: (a) providing a substance modulating activity of a peptide derived from ClCKb protein that is genetically altered at amino acid position 481 compared to the wild type, and (b) formulating said substance Into a pharmaceutically acceptable carrier, wherein step (a) is performed by means of before-mentioned "identifying" method. Herewith it is preferred if said pharmaceutical composition is destined for treatment of hypertension, and/or allergy, and/or hair loss, and/or liability for infection, of a human being. Moreover, a further object of the invention is a pharmaceutical composition prepared by that mentioned method.

Applicable pharmaceutically acceptable carriers are well known in the art; cf. Kibbe, A. H. (2000), Handbook of Pharmaceutical Excipients, $3^{rd}$ edition, American Pharmaceutical Association and Pharmaceutical Press; the content of this handbook is hereby incorporated by reference.

Another object of the present invention relates to a method for treating a human being affected by hypertension, and/or allergy, and/or hair loss, and/or liability for infection, comprising the steps of: (a) providing a genetic construct coding for an antisense-ClCKb$^{T481S}$ probe and/or for a ClCKb$^{T481S}$-RNAi, and (b) introducing said construct into a human being by means of gene therapeutic methods.

This method for the first time enables a causal treatment of a widespread form of hypertension in a direct fashion, i.e. on a genetic level, via so-called antisense technology.

An antisense ClCKb$^{T481S}$ is a genetic construct, i.e. a DNA or RNA sequence, which is complementary to a functional messenger RNA or DNA or to parts thereof, coding for ClCKb$^{T481S}$. This construct is capable of annealing to its complementary structure, thereby blocking translation and/or transcription of that coding region, so that the genetically altered ClCKb protein will not be produced.

ClCKb$^{T481S}$-RNAi stands for ClCKb$^{T481S}$-RNA interference, also called siRNA (for "silencing" RNA), and refers to the introduction of homologous double stranded RNA (dsRNA) to specifically target the RNA coding for ClCKb$^{T481S}$. This measure results in a ClCKb$^{T481S}$ null phenotype. E.g., in a heterozygous person the mutation will be totally suppressed, whereas the wild type ClCKb protein is still active. Although the mechanism of how the dsRNA results in the loss of the targeted homologous mRNA is still not well understood, a number of observations indicate that the primary interference effects are post-transcriptional. Because RNAi is remarkably potent (i.e., only a few dsRNA molecules per cell are required to produce effective interference), the dsRNA must be replicated and/or must work catalytically. The current model favors a catalytic mechanism by which the dsRNA unwinds slightly, allowing the antisense to base pair with a short region of the target endogenous message and marking it for destruction. "Marking" mechanisms could involve covalent modification of the target, i.e. of the mRNA coding for ClCKb$^{T481S}$ (e.g. by adenosine deaminase), or various other mechanisms. Potentially, a single ClCKb$^{T481S}$-RNAi molecule could mark hundreds of target ClCKb$^{T481S}$-mRNAs for destruction before itself is "spent". This technique was discovered by Fire et al. (1998), *Nature* 391, 806–811; the above publication is herewith incorporated by reference.

By the collective term of gene-therapeutic methods, according to the invention those methods are to be understood which cause advantageous changes of a phenotype because of modification or normalization of defect genetic material. Those changes are caused by genes being transfected within cells of specific tissue for there being expressed or to prevent an erroneous or an unregulated expression of the gene.

The afore-mentioned genetic construct can be introduced into a human being by injection in form of "naked" DNA/cDNA or RNA/cRNA, plasmids or vectors, possibly by the usage of modified viruses or transformed bacteria. The genetic construct can also be provided as being included into liposomes, which could be injected or inhaled. In the art, also a gene transfer method is described by which the genetic construct is adsorbed to minute gold particles, which become "shot" into the cells (biolistic method).

Another gene-therapeutic method relates to the so-called ligand-coupled gene transfer. Here, the DNA is coupled to a ligand specific for the target tissue and, therefore, will only be transported into such cells, which carry the appropriate receptor.

In view of the above, in the afore-mentioned method it is preferred if the genetic construct is selected from the group consisting of: naked DNA or cDNA, naked RNA or cRNA, plasmid DNA, plasmid RNA, vector DNA, vector RNA, non-virulent/non-pathogenic virus, transformed bacteria.

This measure has the advantage that the genetic construct will be provided in a form for direct usage in established gene transfer methods.

Due to the potential of the antisense technology, as discussed before, a further object of the present invention is a method for preparing a pharmaceutical composition for treatment of hypertension, and/or allergy, and/or hair loss, and/or liability for infection, comprising the steps of: (a) providing a genetic construct coding for antisense ClCKb$^{T481S}$ and/or ClCKb$^{T481S}$-RNAi, and (b) formulating said construct into a pharmaceutically acceptable carrier, as well as a pharmaceutical composition prepared by that method. A further object of the invention relates to a pharmaceutical composition comprising a genetic construct coding for antisense ClCKb$^{T481S}$, and for ClCKb$^{T481S}$-RNAi, and a pharmaceutically acceptable carrier.

Other advantageous ensue from the description and the attached figure.

It will be understood that the features which are mentioned above, and those which are still to be explained below, can use not only in the combinations which are in each case indicated but also in other combinations, or on their own, without departing from the scope of the present invention.

BRIEF DESCRIPTION OF THE FIGURES

The invention is now explained with the aid of embodiments and the enclosed FIGURE, in which.

DETAILED DESCRIPTION OF PREFERRED EMBODIMENTS

EXAMPLE 1

Screening for the ClCKbT$^{481S}$ Mutation

Figure 1:
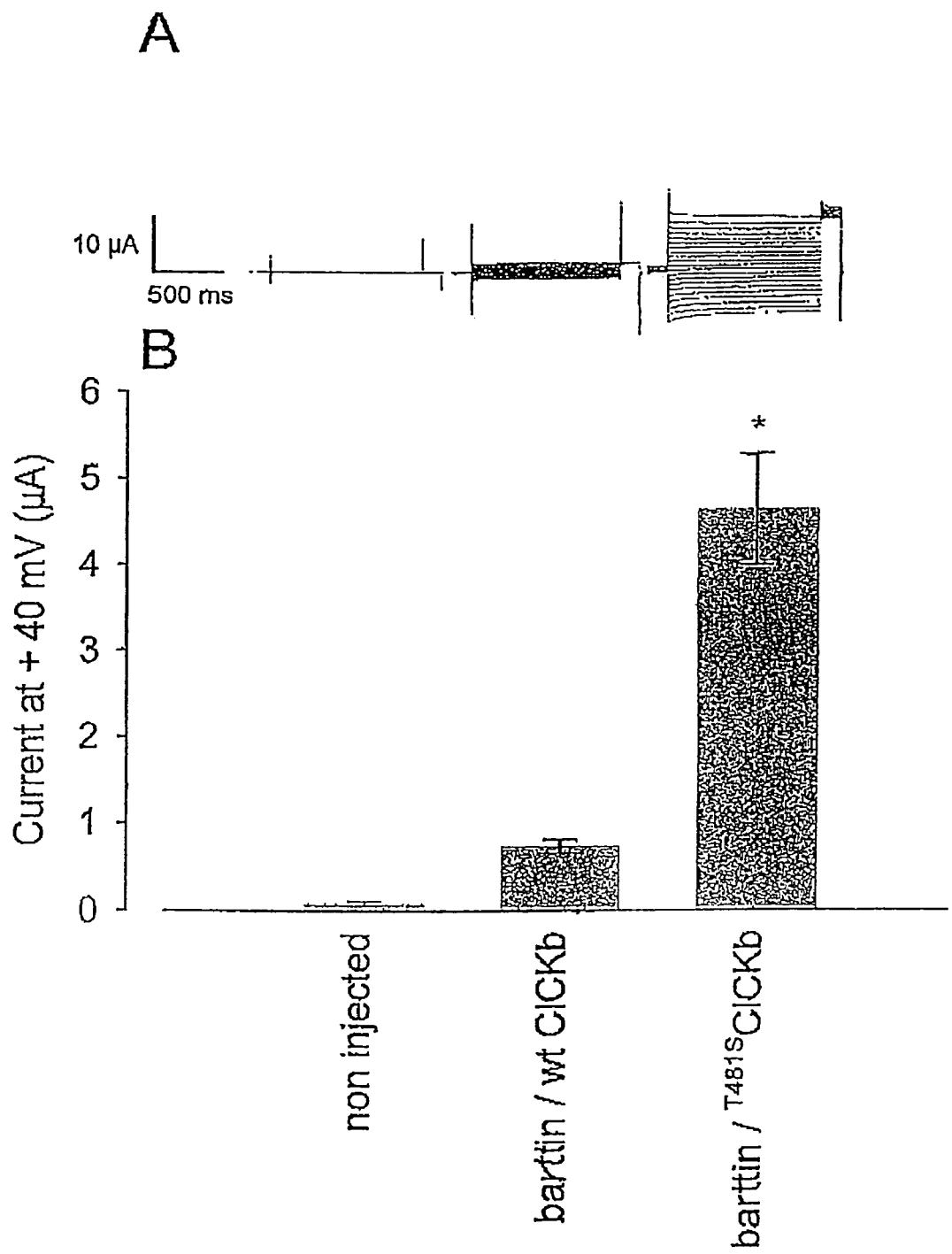
FIG. 1 shows the enhanced conductance of ClCKb$^{T481S}$ as compared to wild type ClCKb.

A population of 198 volunteers (students and employees from the University of Tubingen, age 20–71 years) were recruited and screened for polymorphic variations in the ClCKb gene as described previously; cf. Konrad M. et al. (2000), *J Am Soc Nephrol* 11, 1449–1459. In brief, SSCP (Single Strand Confirmational Polymorphism) analysis was performed on PCR amplified extronic and adjacent intronic ClCKb sequences. Amplification products with apparent SSCP patterns were directly sequenced on both strands.

That screening resulted in the detection of the ClCKb$^{T481S}$ mutation. Four volunteers (2.0%) were homozygous (ClCKb$^{T481S}$/ClCKb$^{T481S}$), 36 volunteers (18.2%) were heterozygous (ClCKb$^{T481S}$/ClCKb), 158 (79.8%) did not carry the mutation (ClCKb/ClCKb). There were no significant differences in gender, age, size, and weight (Table I).

As a result, unlike Liddle's syndrome, the mutation described here is common, affecting some 15–20% of a Caucasian population.

EXAMPLE 2

Blood Pressure Measurements

All volunteers of example 1 have been subjected to blood pressure measurements in a sitting position utilizing an automatic device (Boso Jungingen, Germany). Results concerning blood pressure measurements on heterozygous affected individuals and homozygous individuals carrying exclusively the wild type ClCKb are shown in Table I.

TABLE I

Data of volunteers heterozygous with the ClCKb$^{T481S}$ mutation and of homozygous individuals carrying the wild type ClCKb.

|  | ClCKb$^{T481S}$/ClCKb | ClCKb/ClCKb | t = test |
|---|---|---|---|
| N | 36 (17♀, 19♂) | 158 (77♀, 81♂) | ns |
| age (years) | 33.0 ± 2.3 | 30.0 ± 0.9 | ns |
| size (cm) | 173.3 ± 1.8 | 171.5 ± 1.8 | ns |
| weight (kg) | 67.8 ± 2.2 | 69.8 ± 1.3 | ns |
| RR sys | 138.1 ± 3.1 | 127.8 ± 1.3 | p = 0.0011 |
| RR dias | 84.1 ± 1.6 | 77.8 ± 0.8 | p = 0.0012 |
| n (%) RR ≧ 140/90 | 50% (from 36) | 25% (from 158) | p = 0.012 |

N = number of examined individuals;
RR = blood pressure measured by Riva-Rocci apparatus;
sys = systolic;
dias = diastolic;
n = percentage of individuals having blood pressure exceeding 140/90;
ns = not significant;
p = p-value Both, systolic and diastolic blood pressure were significantly higher in ClCKb$^{T481S}$/ClCKb than in ClCKb/ClCKb. Occurrence of acute hypertension (≧140/90 mmHg) was two fold higher among the carriers of the mutation ClCKb$^{T481S}$/ClCKb (50%) than among individuals without the mutation (ClCKb/ClCKb) (25%). The average blood pressure of 4 homozygous individuals (ClCK$^{T841S}$/ClCKb$^{T481S}$) was similary enhanced (133±7/85±4 mmHg) as compared to that of the heterozygous individuals (not shown in Table I).

As a result, the newly found ClCKb$^{T481S}$ mutation correlates in a statistically well-founded manner with increased blood pressure, i.e. with hypertension.

EXAMPLE 3

ClCKb$^{T481S}$ and Other Disorders

Individuals carrying the ClCKb$^{T481S}$ mutation, both in homozygous as well in heterozygous form, have been questioned for other disturbances of health. Surprisingly, they declared significantly more frequent than other individuals carrying homozygous wild type ClCKb that have also been questioned, that they or their family members are suffering from allergy (p<0.02), or having spare hair growth (p<0.02). Furthermore, the mentioned individuals affected by this mutation have stated as having a tendency for increased liability for infection (p<0.04).

EXAMPLE 4

Functional Studies on Mutated ClCKb$^{T481S}$

In order to analyze whether the newly found mutation alters the activity of the encoded chloride channel Xenopus lavis defolliculated oocytes were injected with cRNA encoding wild type barttin (4 ng/oocyte) together with 4 ng/oocyte of cRNA encoding either wild type ClCKb or ClCKb$^{T481S}$ (side directed mutagenesis was performed with the Quick Change system (stratagene) and the complete constructs were sequenced to prove the desired nucleotide exchange and to exclude any additional mutations).

The oocytes were kept at 16° C. in ND96 storage solution containing 96 mM NaCl, 2 mM KCl, 1.8 mM CaCl$_2$, 1 mM MgCl$_2$, 5 mM HEPES (pH 7.4), 25 mM sodium pyruvate, 0.5 mM theophylline, and 20 µg/ml gentamicin. 2–5 days after injection, two-electrode voltage clamp measurements were performed at room temperature with a GeneClamp 500 amplifier (Axon Instruments).

In that two-electrode voltage-clamp experiments currents were determined utilizing a pulse protocol of 10 s pulses from −140 mV to +40 mV in 20 mV increments. The intermediate holding-voltage was −60 mV. Steady state current at the end of each voltage step were taken for data analysis. The data were filtered at 10 Hz, and recorded with MacLab digital to analogue converter and software for data acquisition and analysis (AD instruments, Castle Hill, Australia). The flow rate of the superfusion of ND96 was 20 ml/min and a complete exchange of the bath solution was reached within about 10 s.

The results of such an experiment are shown in FIG. 1, wherein in part A original tracings on the different oocytes (left: without injected cRNA; middle: with injected barttin and wt ClCKb cRNAs; right: with injected barttin and mutated ClCKb$^{T481S}$cRNA) are shown, and in part B the arithmetic means ±SEM of currents are shown. * indicates significant difference between currents in oocytes expressing wt ClCKb or ClCKb$^{T481S}$.

As can be taken from the data presented in FIG. 1, the ClCKb$^{T481S}$ mutation leads to a gain-of-function mutation, since introducing the mutated channel protein into Xenopus oocytes leads to almost 7 fold increase of ClCKb induced currents, cf. FIG. 1B right column compared to the column in the middle.

In conclusion the inventors have been able to show that a genetic alteration in human ClCKb protein at amino acid position 481 leads to an increased activity of the encoded chloride channel and therefore causes hypertension, allergy, hair loss and a liability for infection. Therefore, the newly found genetic alteration is a useful diagnostic and therapeutic target for the management of the mentioned disorders.

Therefore, what is claimed, is:

1. A method for diagnosing hypertension in a human being. or a predisposition for hypertension in a human being, comprising
   (a) providing a biological sample of said human being;
   (b) analyzing said biological sample for a nucleic cid molecule encoding chloride channel Kb (ClCkb) protein comprising a genetic alteration at amino acid position Thr481 compared to wild-type human ClCkb; and
   (c) correlating the positive findings of the nucleic acid encoding chloride channel Kb (ClCKb) protein comprising a genetic alteration at amino acid position 481 with hypertension.

2. The method according to claim 1, wherein said analyzing for the presence of said nucleic acid molecule in step (b) is performed by means of PCR technology.

3. The method according to claim 2, wherein the PCR amplification products are analyzed by means of denaturing high pressure liquid chromatography (dHPLC).

4. The method of claim 1, wherein the ClCKb protein comprises the amino acid alteration of Thr481 to seine.

5. A method for diagnosing hypertension in a human being. or a predisposition for hypertension in a human being, comprising
   (a) providing a biological sample of said human being;
   (b) analyzing said biological sample for chloride channel Kb (ClCKb) protein comprising a genetic alteration at amino acid position Thr481 compared to wild-type human ClCKb; and
   (c) correlating the positive findings of the chloride channel Kb (ClCKb) protein comprising a genetic alteration at amino acid position 481 with hypertension.

6. The method of claim 5, wherein the ClcKb protein comprises the amino acid alteration of Thr481 to seine.

* * * * *

UNITED STATES PATENT AND TRADEMARK OFFICE
CERTIFICATE OF CORRECTION

PATENT NO. : 7,235,364 B2  Page 1 of 1
APPLICATION NO. : 11/398208
DATED : June 26, 2007
INVENTOR(S) : Lang et al.

It is certified that error appears in the above-identified patent and that said Letters Patent is hereby corrected as shown below:

Col. 15 line 2, please delete "seine" and insert --serine-- therefore.

Col. 16 line 7, please delete "seine" and insert --serine-- therefore.

Signed and Sealed this

First Day of April, 2008

JON W. DUDAS
*Director of the United States Patent and Trademark Office*

SEQUENCE LISTING

<160> NUMBER OF SEQ ID NOS: 1

<210> SEQ ID NO 1
<211> LENGTH: 687
<212> TYPE: PRT
<213> ORGANISM: Homo sapiens

<400> SEQUENCE: 1

```
Met Glu Glu Phe Val Gly Leu Arg Gly Ser Ser Gly Asn Pro Val
 1               5                  10                  15

Thr Leu Gln Glu Leu Trp Gly Pro Cys Pro Leu Ile Arg Arg Gly Ile
                20                  25                  30

Arg Gly Gly Leu Glu Trp Leu Lys Gln Lys Leu Phe Arg Leu Gly Glu
                35                  40                  45

Asp Trp Tyr Phe Leu Met Thr Leu Gly Val Leu Met Ala Leu Val Ser
     50                  55                  60

Cys Ala Met Asp Leu Ala Val Glu Ser Val Val Arg Ala His Gln Trp
 65              70                  75                  80

Leu Tyr Arg Glu Ile Gly Asp Ser His Leu Leu Arg Tyr Leu Ser Trp
                85                  90                  95

Thr Val Tyr Pro Val Ala Leu Val Ser Phe Ser Ser Gly Phe Ser Gln
                100                 105                 110

Ser Ile Thr Pro Ser Ser Gly Gly Ser Gly Ile Pro Glu Val Lys Thr
                115                 120                 125

Met Leu Ala Gly Val Val Leu Glu Asp Tyr Leu Asp Ile Lys Asn Phe
    130                 135                 140

Gly Ala Lys Val Val Gly Leu Ser Cys Thr Leu Ala Cys Gly Ser Thr
145                 150                 155                 160

Leu Phe Leu Gly Lys Val Gly Pro Phe Val His Leu Ser Val Met Met
                165                 170                 175

Ala Ala Tyr Leu Gly Arg Val Arg Thr Thr Thr Ile Gly Glu Pro Glu
                180                 185                 190

Asn Lys Ser Lys Gln Asn Glu Met Leu Val Ala Ala Ala Val Gly
                195                 200                 205

Val Ala Thr Val Phe Gly Ala Pro Phe Ser Gly Val Leu Phe Ser Ile
    210                 215                 220

Glu Val Met Ser Ser His Phe Ser Val Trp Asp Tyr Trp Arg Gly Phe
225                 230                 235                 240

Phe Ala Ala Thr Cys Gly Ala Phe Met Phe Arg Leu Leu Ala Val Phe
                245                 250                 255

Asn Ser Glu Gln Glu Thr Ile Thr Ser Leu Tyr Lys Thr Ser Phe Arg
                260                 265                 270

Val Asp Val Pro Phe Asp Leu Pro Glu Ile Phe Phe Val Val Leu
    275                 280                 285

Gly Gly Leu Cys Gly Ile Leu Gly Ser Ala Tyr Leu Phe Cys Gln Arg
    290                 295                 300

Ile Phe Phe Gly Phe Ile Arg Asn Asn Arg Phe Ser Lys Leu Leu
305                 310                 315                 320

Ala Thr Ser Lys Pro Val Tyr Ser Ala Leu Ala Thr Leu Val Leu Ala
                325                 330                 335
```

-continued

```
Ser Ile Thr Tyr Pro Pro Ser Ala Gly Arg Phe Leu Ala Ser Arg Leu
            340             345             350

Ser Met Lys Gln His Leu Asp Ser Leu Phe Asp Asn His Ser Trp Ala
        355             360             365

Leu Met Thr Gln Asn Ser Ser Pro Pro Trp Pro Glu Glu Leu Asp Pro
        370             375             380

Gln His Leu Trp Trp Glu Trp Tyr His Pro Arg Phe Thr Ile Phe Gly
385             390             395                         400

Thr Leu Ala Phe Phe Leu Val Met Lys Phe Trp Met Leu Ile Leu Ala
                405             410             415

Thr Thr Ile Pro Met Pro Ala Gly Tyr Phe Met Pro Ile Phe Val Tyr
            420             425             430

Gly Ala Ala Ile Gly Arg Leu Phe Gly Glu Thr Leu Ser Phe Ile Phe
            435             440             445

Pro Glu Gly Ile Val Ala Gly Gly Ile Thr Asn Pro Ile Met Pro Gly
        450             455             460

Gly Tyr Ala Leu Ala Gly Ala Ala Phe Ser Gly Ala Val Thr His
465             470             475             480

Thr Ile Ser Thr Ala Leu Leu Ala Phe Glu Val Thr Gly Gln Ile Val
            485             490             495

His Ala Leu Pro Val Leu Met Ala Val Leu Ala Ala Asn Ala Ile Ala
            500             505             510

Gln Ser Cys Gln Pro Ser Phe Tyr Asp Gly Thr Val Ile Val Lys Lys
        515             520             525

Leu Pro Tyr Leu Pro Arg Ile Leu Gly Arg Asn Ile Gly Ser His Arg
        530             535             540

Val Arg Val Glu His Phe Met Asn His Ser Ile Thr Thr Leu Ala Lys
545             550             555             560

Asp Thr Pro Leu Glu Glu Val Val Lys Val Val Thr Ser Thr Asp Val
            565             570             575

Ala Glu Tyr Pro Leu Val Glu Ser Thr Glu Ser Gln Ile Leu Val Gly
            580             585             590

Ile Val Arg Arg Ala Gln Leu Val Gln Ala Leu Lys Ala Glu Pro Pro
        595             600             605

Ser Trp Ala Pro Gly His Gln Gln Cys Leu Gln Asp Ile Leu Ala Ala
        610             615             620

Gly Cys Pro Thr Glu Pro Val Thr Leu Lys Leu Ser Pro Glu Thr Ser
625             630             635             640

Leu His Glu Ala His Asn Leu Phe Glu Leu Leu Asn Leu His Ser Leu
            645             650             655

Phe Val Thr Ser Arg Gly Arg Ala Val Gly Cys Val Ser Trp Val Glu
            660             665             670

Met Lys Lys Ala Ile Ser Asn Leu Thr Asn Pro Pro Ala Pro Lys
        675             680             685
```